United States Patent [19]

Kurze et al.

[11] Patent Number: 4,832,602

[45] Date of Patent: May 23, 1989

[54] STOMATOLOGICAL IMPLANT

[75] Inventors: Peter Kurze, Oberlichtenau; Rabending, Klaus, Taura; Waldemar Krysmann, Karl Marx Stadt; Gerold Loewicke, Erfurt; Wolfram Knofler; Hans-Ludwig Graf, both of Leipzig, all of German Democratic Rep.

[73] Assignee: Technische Universitaet Karl-Marx-Stadt, Karl Marx Stadt, Fed. Rep. of Germany

[21] Appl. No.: 151,365

[22] Filed: Feb. 2, 1988

[30] Foreign Application Priority Data

Feb. 2, 1987 [DD] German Democratic Rep. ... 299621

[51] Int. Cl.$^4$ .............................................. A61C 5/08
[52] U.S. Cl. .................................................. 433/220
[58] Field of Search ............... 433/220, 201, 173, 174, 433/175, 176, 224

[56] References Cited

U.S. PATENT DOCUMENTS

| 4,283,176 | 8/1981 | Vajda | 433/220 |
| 4,408,990 | 10/1983 | Misch | 433/220 |
| 4,600,391 | 7/1986 | Jacob | 433/220 |

Primary Examiner—Robert Peshock
Attorney, Agent, or Firm—Jordan and Hamburg

[57] ABSTRACT

The invention relates to a stomatological implant in the form of selectively coated root canal pins, short pins, transfixion pins, replantation pins, of titanium, tantalum, niobium, zirconium and/or their alloys. The stomatological implant is used for long-term bacteria-proof closure of the root canal. Pursuant to the invention, up to three zones may be selectively put on the implant, meeting a variety of biological requirements.

11 Claims, 1 Drawing Sheet

STOMATOLOGICAL IMPLANT

BACKGROUND OF THE INVENTION

The invention relates to a stomatological implant of titanium, tantalum, niobium, zirconium and/or their alloys for use as a root-canal pin; more particularly, the invention concerns stomatological implants such as biocompatible metals which are useful as transfixion pins, replantation pins or root-filling pins, in particular short pins.

It is known that root-canal pins of Ti, Ta, etc. may be used in stomatology in root-canal treatments and transfixions and apical root resections. In doing so, the root canal is prepared true to shape and the root-canal pin is inserted with the use of a more or less compatible hardening filling material (cements, epoxy resins), as may be gathered from, for example, the prospectus of the firm of Institut Straumann AG, CH-4437 Waldenburg, "Apikaler Wurzelkanalstift aus Titan" (Apical Root-Canal Pin of Titanium). Despite this technique, used for years in stomatology, the development of macrocracks between root-canal pin and tooth substance owing to incomplete filling or rinsing out of the root-filling material serving as packing compound cannot be prevented (Deutsche zahnärtztliche Zeitschrift 42 (1987), pp. 262–264, 277–282). On the other hand, filling materials to which insolubility is attributed are not very osteocompatible. Hence, the known complications appear, ultimately leading to the loss of the tooth.

SUMMARY OF THE INVENTION

The object of the invention is to procure a root canal pin whose surface is properly adapted to the functions to be performed by the implant which include:
long-term bacteria-proof closure of the root canal, without additional sealing materials
osteocompatibility
automatic cutting advance into the bone.

Pursuant to the invention, the object is accomplished by the discovery of a stomatological implant, the fundamental implant substance of which consists of at least one biocompatible metal, in particular titanium, tantalum, niobium, zirconium or their alloys, and, depending upon its function as a root filling pin and/or transfixion pin and according to the biological environment, is divided into zones, with regard to shape and the nature of the surface.

Zone I comprises a truncated cone to be firmly anchored in the root canal, whose surface is covered with a biocompatible ANOF layer, which refers to a layer produced by anodic oxidation by spark discharge, up to 40 μm thick and softer than the apical region, which layer is abraded upon introduction into the prepared root canal, resulting in a sealing effect. (ANOF is a term of art as shown, for example, by cryst. Res. Technol. 21 (1986) 1603–1609.)

Zone II comprises the cylindrical part of the implant and bears a nonabradable ANOF layer up to 10 μm thick and harder with respect to the biological environment, which layer contains up to 40% of osteogenesis-stimulating calcium and phosphate ions and has a relative pore areas of less than 15%.

Zone III comprises the pointed portion of the implant, the surface of which is covered with a biocompatible oxide and/or nitride and/or carbide layer up to 5 μm thick and upon implantation assumes the function of a drill.

The implant may selectively be provided with only one, with two or with all three zones, depending upon the purpose for which it is to be used.

As a short pin, for example, only Zone I is required. As a transfixion pin, all three zones described (I-III) are necessary. As a replantation pin, on the other hand, Zones I and II are sufficient. After the root canal is prepared true to shape, the root canal pin is screwed in according to the known manner, without filling material. When Zones III and II are worked into the jaw bone, because of the structure of the separate zones pursuant to the invention, no dust is to be noted between implant and bone and, owing to the calcium and phosphate content of Zone II, incorporation into the bone substance is favorably influenced.

The advantages obtained by the invention include the guarantee that these implants provide a long-term bacteria-proof closure of the root canal without additional sealing materials.

BRIEF DESCRIPTION OF THE DRAWINGS

The invention is explained in detail by two examples, wherein.

DETAILED DESCRIPTION OF THE PREFERRED EMBODIMENTS

Figure 1:
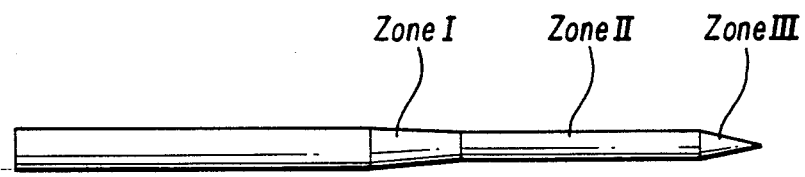
FIG. 1 shows a transfixion pin and
FIG. 2, a short pin.

FIG. 1 represents a transfixion pin of EMO titanium 110 with a total length of 25 mm, having a Zone I, which is a truncated cone of the: diameters $d_1 = 1.2$ mm, $d_2 = 1.0$ mm and height $h = 3$ mm and which, is coated with an ANOF layer produced in an electrolyte of the composition 0.5 mol/l NaF, 0.5 mol/l $NaH_2PO_4$, 0.1 mol/l $Na_2B_4O_7$, 0.1 mol/l $NH_4F$, up to a thickness of 25 μm. The threadbearing cylindrical Zone II has a diameter of 1.0 mm and a length of 8 mm and is covered with an 8 μm-thick ANOF layer, formed in an aqueous, saturated $Ca(HPO_4)_2$ electrolyte. The calcium phosphate concentration on the surface of the layer amounts to 30%.

Zone III is pointed in shape, with a basal diameter of 0.8 mm and a height of 2.0 mm, and the surface thereof is covered with a 2 μm-thick titanium-oxide layer. The transfixion pin of the invention is medically advantageous in that, owing to the abradable titanium oxide particles of Zone I, the roughnesses of the root canal surface are closed up and a long-lasting stable bacteria-proof closure is thereby obtained.

Figure 2:
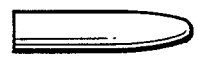

FIG. 2 represents a projectile-shaped short pin of 6 mm in length, a basal diameter of 1.2 mm and a parabolic longitudinal section, which is coated with an ANOF layer produced by means of an electrolyte of the composition 0.5 mol/l NaF, 0.5 mol/l $NaH_2PO_4$, 0.1 mol/l $Na_2B_4O_7$ and 0.1 mol/l $NH_4F$ up to a thickness of 25 nm. This pin is inserted cement-free after root canal resection and root-canal preparation true to shape.

We claim:
1. A stomatological implant comprising a root canal pin composed of at least one biocompatible metal selected from titanium, tantalum, niobium, zirconium and alloys thereof comprising
a Zone I which is a truncated cone to be firmly anchored in a root canal covered with a biocompatible ANOF layer softer than the apical region and which is abraded upon introduction into the root canal, a Zone II adjoining Zone I having a cylindrical body covered with a nonabradable ANOF layer harder than the biological environment with which it will be in contact and a Zone II adjoining Zone II having a pointed end section covered with a surface layer selected from at least one member of the group consisting of biocompatible oxide, biocompatible nitride and biocompatible carbide.

2. The stomatological implant according to claim 1, in which the ANOF layer of Zone I has a thickness of up to 40 μm.

3. The stomatological implant according to claim 1, in which the ANOF layer of Zone II has a thickness of up to 10 μm.

4. The stomatological implant according to claim 1, in which the ANOF layer of Zone II contains up to 40% of osteogenesis-stimulating calcium and phosphate ions.

5. The stomatological implant according to claim 1, in which the surface layer of Zone III has a thickness of up to 5 μm.

6. A stomatological implant useful as a replantation pin, composed of at least one biocompatible metal selected from titanium, tantalum, niobium, zirconium and alloys thereof comprising a Zone I which is a truncated cone to be firmly anchored in a root canal covered with a biocompatible ANOF layer softer than the apical region and a Zone II adjoining Zone I having a cylindrical body covered with a nonabradable ANOF layer harder than the biological environment with which it will be in contact.

7. The stomatological implant according to claim 6, in which the ANOF layer of Zone I has a thickness of up to 40 μm.

8. The stomatological implant according to claim 6, in which the ANOF layer of Zone II has a thickness of up to 10 μm.

9. The stomatological implant according to claim 6, in which the ANOF layer of Zone II contains up to 40% of osteogenesis-stimulating calcium and phosphate ions.

10. A stomatological implant pin composed of at least one biocompatible metal selected from titanium, tantalum, niobium, zirconium and alloys thereof comprising a projectile shaped pin capable of being firmly anchored in a root canal and provided with a covering of a biocompatible ANOF layer softer than the apical region.

11. The stomatological implant according to claim 10, in which the ANOF layer has a thickness of up to 40 μm.

* * * * *